(12) United States Patent
Kurnik et al.

(10) Patent No.: US 8,095,322 B2
(45) Date of Patent: Jan. 10, 2012

(54) SYSTEMS AND METHODS FOR DETERMINING CROSS-TALK COEFFICIENTS IN PCR AND OTHER DATA SETS

(75) Inventors: Ronald Kurnik, Foster City, CA (US); Aditya Sane, Pleasanton, CA (US); Christopher Elkin, San Ramon, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 474 days.

(21) Appl. No.: 12/163,445

(22) Filed: Jun. 27, 2008

(65) Prior Publication Data

US 2009/0035779 A1 Feb. 5, 2009

Related U.S. Application Data

(60) Provisional application No. 60/947,065, filed on Jun. 29, 2007.

(51) Int. Cl.
*G01N 33/48* (2006.01)
(52) U.S. Cl. ......................................... 702/19
(58) Field of Classification Search .................. None
See application file for complete search history.

(56) References Cited

U.S. PATENT DOCUMENTS

| | | | |
|---|---|---|---|
| 5,606,164 A * | 2/1997 | Price et al. | 250/339.09 |
| 2002/0042051 A1 * | 4/2002 | Wittwer | 435/6 |
| 2004/0259260 A1 | 12/2004 | Gunstream et al. | |
| 2007/0143385 A1 | 6/2007 | Kurnik et al. | |
| 2007/0148632 A1 | 6/2007 | Kurnik et al. | |
| 2007/0166744 A1 * | 7/2007 | Knobel | 435/6 |
| 2008/0018898 A1 * | 1/2008 | Gunstream et al. | 356/416 |

FOREIGN PATENT DOCUMENTS

WO    WO 02/086416 A2    10/2002

OTHER PUBLICATIONS

Huang, W. et al., "Filter Matrix Estimation in Automated DNA Sequencing," *IEEE Transactions on Biomedical Engineering*, Apr. 1998, vol. 45, No. 4, pp. 422-428.
Li et al., "An estimate of the crosstalk matrix in four-dye fluorescence-based DNA sequencing," *Electrophoresis*, 1999, vol. 20, pp. 1433-1442.
International Search Report mailed on Oct. 31, 2008, for PCT Application No. PCT/EP2008/005255 filed on Jun. 27, 2008, 4 pages.

* cited by examiner

*Primary Examiner* — Jason Sims
(74) *Attorney, Agent, or Firm* — Kilpatrick Townsend & Stockton LLP; Gerald T. Gray

(57) ABSTRACT

Systems and methods for determining cross-talk coefficients in curves, such as sigmoid-type or growth curves, and PCR curves and nucleic acid melting curves in particular, as well as for applying the cross-talk coefficients to produce cross-talk corrected data sets using a linear subtractive model. Cross-talk signal coefficients are determined using cross-talk data acquired across the entire signal acquisition range. Analyzing across all of the signal curve data provides for a more robust cross-talk correction across the entire data acquisition range. A linear subtractive model is used to correct data sets having cross-talk components.

21 Claims, 10 Drawing Sheets

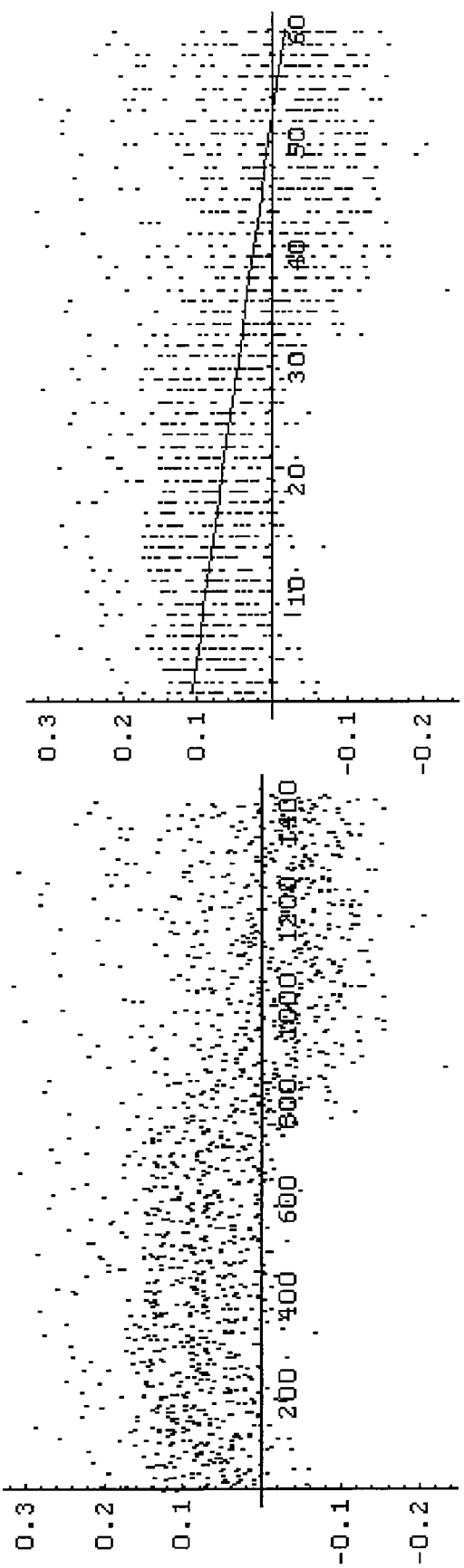

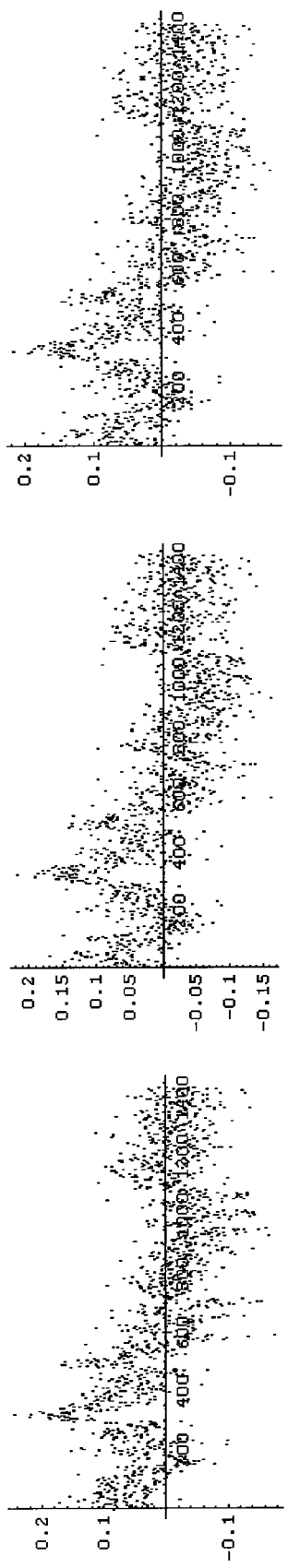

HIV in FAM channel

Cross-talk of HIV in HEX channel

SYSTEMS AND METHODS FOR DETERMINING CROSS-TALK COEFFICIENTS IN PCR AND OTHER DATA SETS

CROSS-REFERENCES TO RELATED APPLICATIONS

The present application claims priority to and is a nonprovisional application of U.S. Provisional Patent Ser. No. 60/947,065 filed Jun. 29, 2007. The disclosure of which is hereby incorporated by reference in its entirety for all purposes.

BACKGROUND OF THE INVENTION

The present invention relates generally to systems and methods for processing data representing sigmoid-type or growth curves such as Polymerase Chain Reaction (PCR) curves, and more particularly to systems and methods for determining cross-talk characteristics of PCR detection systems.

The Polymerase Chain Reaction (PCR) is an in vitro method for enzymatically synthesizing or amplifying defined nucleic acid sequences. The reaction typically uses two oligonucleotide primers that hybridize to opposite strands and flank a template or target DNA sequence that is to be amplified. Elongation of the primers is catalyzed by a heat-stable DNA polymerase. A repetitive series of cycles involving template denaturation, primer annealing, and extension of the annealed primers by the polymerase results in an exponential accumulation of a specific DNA fragment. Fluorescent probes are typically used in the process to facilitate detection and quantification of the amplification process.

A set of typical real-time PCR curves is shown in FIG. 1a, where fluorescence intensity values are plotted vs. cycle number for a typical PCR process. In this case, the formation of PCR products is monitored in each cycle of the PCR process. The amplification is usually measured in thermocyclers which include components and devices for measuring fluorescence signals during the amplification reaction. An example of such a thermocycler is the Roche Diagnostics LightCycler (Cat. No. 20110468). The amplification products are, for example, detected by means of fluorescent labelled hybridization probes which emit fluorescence signals when they are bound to the target nucleic acid or in certain cases also by means of fluorescent dyes that bind to double-stranded DNA. As can be seen in FIG. 1a, the PCR curves include a baseline region 5 and a plateau region 6. The region between the baseline region 5 and the plateau region 6 is typically referred to as the growth region.

Typical PCR detection systems for analyzing radiation emissions from PCR experiments include two or more filters that are each operable to isolate a wavelength range for further analysis. For example, each optical filter typically allows substantially all radiation in a defined wavelength range to pass. However, the probes or markers typically emit with partially overlapping wavelength bands, and a filter's band pass typically includes a region of this overlap such that each detection channel will typically receive signal emitted from other probes. Such cross-talk signals tend to affect the real signal of interest. Accordingly, it is desirable to correct for such cross-talk signals in each detection channel. One traditional way of doing this is to determine quantitative cross-talk coefficients that can be used to correct for cross-talk signals in each detection channel.

In current cross-talk methodologies, the cross-talk coefficients are typically calculated using a ratio of the average plateau values of a basis and cross-talk signal; conventional methods rely exclusively on the plateau region which contains less than 10% of the data. Also, during PCR, the plateau region signal is generated when the chemistry is in an unstable state. For this reason, a baseline signal threshold is typically employed for target identification. Therefore, the conventional methods use a noisy signal to determine cross-talk coefficients with limited information that does not include data from the true signal acquisition region on the curve. Further, incorrect assumptions used in conventional crosstalk models have also been found to induce errors as a function of the data acquisition curve. Thus, the conventional method of calculating cross-talk coefficients may be satisfactory providing that (1) a plateau exists, (2) the plateau is flat, and (3) there is minimum noise in the plateau. However, there are many data sets where this will not be the case.

It is therefore desirable to provide systems and methods for determining cross-talk coefficients in curves, such as sigmoid-type or growth curves, and PCR curves in particular, which overcome the above and other problems.

BRIEF SUMMARY OF THE INVENTION

The present invention provides systems and methods for determining cross-talk coefficients in curves, such as sigmoid-type or growth curves, and PCR curves in particular. The present invention also provides systems and methods for applying the cross-talk coefficients to produce cross-talk corrected data sets using a linear subtractive model.

According to various embodiments, cross-talk signal coefficients are determined by minimizing the sum of the squares of the difference between a basis signal (times a gain and optionally plus a linear term) and a cross-talk signal. This technique has been shown to be superior to conventional techniques that use a ratio of the average plateau values of a basis and cross-talk signal. Additionally, this technique analyzes data across the entire signal acquisition range to determine cross-talk coefficients. For example, all data across the acquisition range may be used, or portions of data across the entire acquisition range may be used. Analyzing across all of the signal curve data provides for a more robust cross-talk correction across the entire data acquisition range. In addition, conventional methods assume that measured signals from all sources are a linear additive model and that all signals are parsed between the detectors; this is not true, and results in both over and under corrections of the resultant signal. The techniques of the present invention instead use a linear subtractive model which overcomes this issue and better models the actual detection system. These new techniques will find their greatest utility in examples where the cross-talk coefficients are in the range of 2% or larger.

According to one aspect of the present invention, a method is provided for determining cross-talk coefficients for a Polymerase Chain Reaction (PCR) optical detection system having at least two optical elements, each optical element operable to isolate a different specific electromagnetic wavelength range. The method typically includes acquiring, for each optical element, a PCR data set over an acquisition range of a PCR growth process, and simultaneously acquiring, for each other optical element, a cross-talk data set over the acquisition range. The method further typically includes determining cross-talk coefficients using the PCR and cross-talk data sets. In certain aspects, the acquisition range includes a baseline region, a growth region and a plateau region. In certain aspects, determining the cross-talk coefficients includes minimizing a sum of the squares between each PCR data set and cross-talk data set over the acquisition range. In certain aspects, the cross-talk coefficients are applied to a PCR data set to produce a cross-talk corrected PCR data set. In certain aspects, a linear subtractive model is used to apply the cross-talk coefficients.

According to another aspect of the present invention, a computer readable medium is provided that includes or stores code for controlling a processor to determine cross-talk coefficients for a Polymerase Chain Reaction (PCR) optical detection system having at least two optical elements, each optical element operable to isolate a different specific electromagnetic wavelength range. The code typically includes instructions to receive, for each optical element, a PCR data set acquired over an acquisition range of a PCR growth process, and simultaneously receive, for each other optical element, a cross-talk data set for each filter acquired over the acquisition range. The code also typically includes instructions to determine cross-talk coefficients using the PCR and cross-talk datasets. In certain aspects, the acquisition range includes a baseline region, a growth region and a plateau region. In certain aspects, the code to determine the cross-talk coefficients includes code to determine cross-talk coefficients by minimizing a sum of squares between each PCR data set and cross-talk data set over the acquisition range.

According to yet another aspect of the present invention, a kinetic Polymerase Chain Reaction (PCR) system is provided that typically includes an optical detection module having at least two optical elements, each optical element operable to isolate a different specific electromagnetic wavelength range, wherein the optical detection module is typically adapted to acquire, for each optical element, a PCR data set over an acquisition range of a PCR growth process, and simultaneously acquire, for each other optical element, a cross-talk data set over the acquisition range. The system also typically includes an intelligence module adapted to process the acquired PCR data sets and cross-talk data sets to determine cross-talk coefficients. In certain aspects, the acquisition range includes a baseline region, a growth region and a plateau region. In certain aspects, the intelligence module determines the cross-talk coefficients by minimizing a sum of squares between each PCR data set and cross-talk data set over the acquisition range.

According to yet a further aspect of the present invention, a nucleic acid melting analysis system is provided that typically includes an optical detection module having at least two optical elements, each optical element operable to isolate a different specific electromagnetic wavelength range. Typically, the optical detection module is adapted to acquire, for each optical element, a melting data set over a temperature acquisition range, and simultaneously acquire, for each other optical element, a cross-talk data set over the temperature acquisition range. The optical detection module is also typically adapted to determine cross-talk coefficients by minimizing a sum of squares between each melting data set and cross-talk data set over the acquisition range.

According to still a further aspect of the present invention, a method is provided for determining cross-talk coefficients for an optical detection system having at least two optical elements, each optical element operable to isolate a different specific electromagnetic wavelength range. The method typically includes acquiring, for each optical element, a first data set over an acquisition range of a growth process, simultaneously acquiring, for each other optical element, a cross-talk data set over the acquisition range, and determining cross-talk coefficients using the first and cross-talk data sets over the acquisition range. The growth process, in certain aspects, is one of a PCR process, a bacterial process, an enzymatic process or a binding process.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 5 shows the twenty-four plots of FIG. 24 end-to-end.

FIG. 6 shows a superposition of all twenty-four plots of FIG. 4.

FIGS. 7-9 show the end-to-end residual plots for a data set processed according to embodiments of the present invention.

FIGS. 10-12 show the superimposed residual plots corresponding to plots shown in FIGS. 7-9, respectively.

DETAILED DESCRIPTION OF THE INVENTION

The present invention provides systems and methods for determining cross-talk coefficients and for producing cross-talk corrected data sets using the cross-talk coefficients, particularly for PCR detection systems and PCR data sets, and nucleic acid melting data sets. The present invention also provides systems and methods for applying the cross-talk coefficients to produce cross-talk corrected data sets using a linear subtractive model.

Although the remainder of this document will discuss embodiments and aspects of the invention in terms of its applicability to PCR data sets, it should be appreciated that the present invention may be applied to data sets related to other processes. Examples of other processes that may provide similar sigmoid-type or growth curves, or which may otherwise be processed according to the techniques of the present invention include bacterial processes, melting processes, microbial growth processes, enzymatic processes (e.g., enzymatic kinetic reactions) and binding processes. For example, the techniques of the present invention are also applicable to analyzing data from nucleic acid melting processes and similar processes.

Figure 1A:
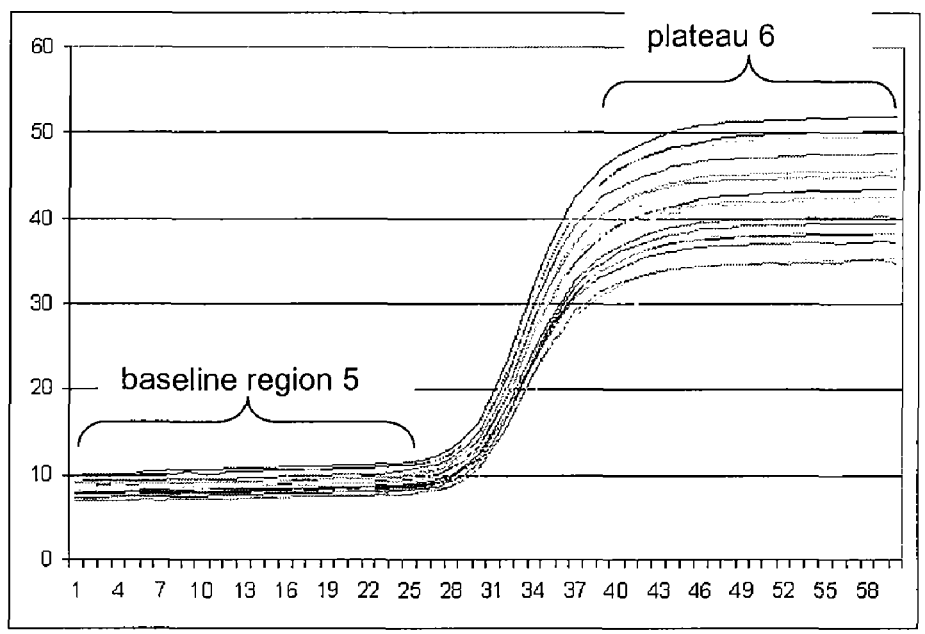
FIG. 1a illustrates a set of typical real-time PCR curves, where fluorescence intensity values are plotted vs. cycle number for a typical PCR process.

As shown in FIG. 1a, data for a typical PCR growth curve can be represented in a two-dimensional coordinate system, for example, with PCR cycle number defining the x-axis and an indicator of accumulated polynucleotide growth defining the y-axis. Typically, as shown in FIG. 1a, the indicator of accumulated growth is a fluorescence intensity value as the use of fluorescent markers is perhaps the most widely used labeling scheme. However, it should be understood that other indicators may be used depending on the particular labeling and/or detection scheme used. Examples of other useful indicators of accumulated signal growth include luminescence intensity, chemiluminescence intensity, bioluminescence intensity, phosphorescence intensity, charge transfer, voltage, current, power, energy, temperature, viscosity, light scatter, radioactive intensity, reflectivity, transmittance and absorbance. The definition of cycle can also include time, process cycles, unit operation cycles and reproductive cycles.

General Process Overview

Figure 1B:
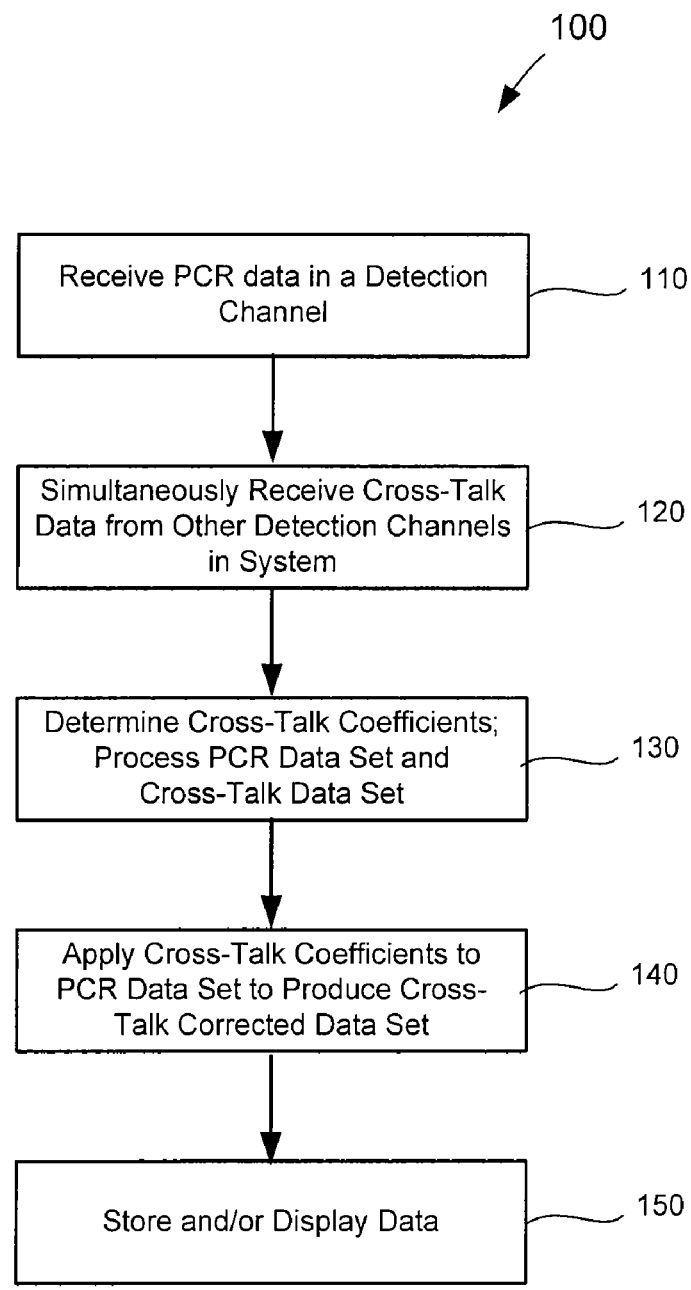
FIG. 1b illustrates a process for determining cross-talk coefficients for a detection system that analyzes PCR amplification processes using two or more detection channels.

According to the present invention, one embodiment of a process 100 for determining cross-talk coefficients for a detection system that analyzes PCR amplification processes using two or more detection channels can be described briefly with reference to FIG. 1b. In certain aspects, a PCR detection system includes detectors for analyzing radiation emissions from PCR experiments. The detection system includes two or more optical elements that are each operable to isolate a wavelength range for further analysis. These optical elements are usually selected to match the emission characteristics of the fluorescent probes or markers used in PCR amplification processes, e.g., isolate radiation within the emission band of a particular dye. For example, in certain aspects, the optical elements include one or more optical filters that allow substantially all radiation in a defined wavelength range to pass. Other optical elements might include diffraction gratings. Each optical element defines a detection channel, e.g., a wavelength range that is received by a detector element.

Figure 2B:
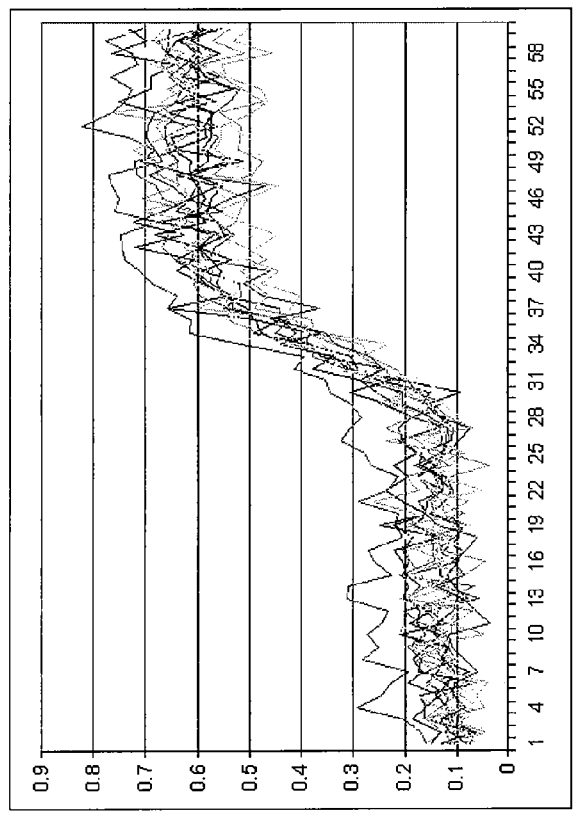
FIG. 2 illustrates a specific two-channel case: the FAM signal and its cross-talk into the HEX channel for a two channel detection system.
Figure 2A:
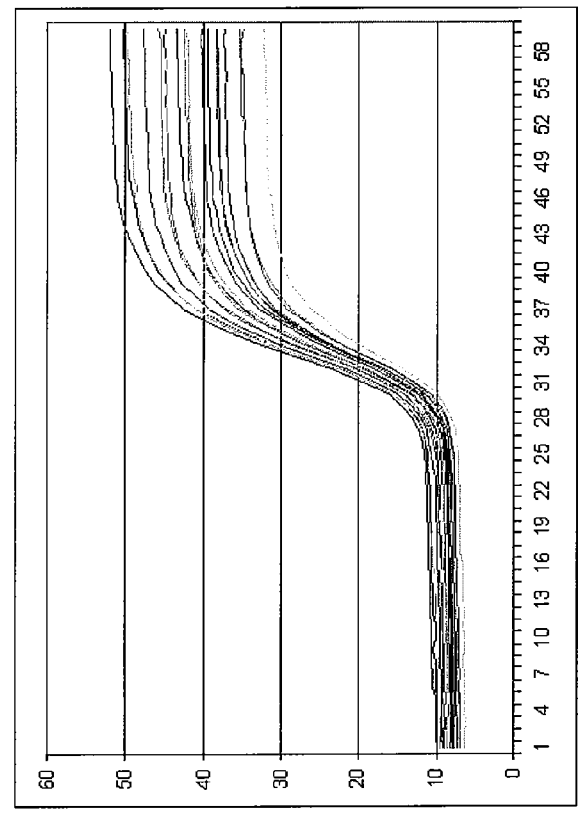

In step 110, for each detection channel, an experimental data set representing one or more PCR curves is received or otherwise acquired. In certain aspects, data is acquired across the entire acquisition range of the detection system, e.g., across the baseline region, the transition region and the plateau region. An example of a plotted PCR data set (set of one or more PCR data curves) is shown in FIG. 2A, where the y-axis and x-axis represent fluorescence intensity and cycle number, respectively, for a PCR curve. In certain aspects, the data set should include data that is equally spaced along an axis. However, there may be one or more missing data points. In step 120, simultaneously with step 110, for each other channel, a cross talk data set is acquired over the acquisition range. An example of a cross-talk data set is shown in FIG. 2B. In step 130, the data sets are processed to determine cross talk coefficients as will be described in more detail below. In certain aspects, a sum of the squares between each PCR data set and cross talk data set is minimized as will be described below. In other aspects, a sum of the absolute values of the difference between the PCR data set and the cross-talk data set is minimized.

In the case where process 100 is implemented in an intelligence module (e.g., processor executing instructions) resident in a PCR data acquiring device such as a thermocycler, the data set may be provided to the intelligence module in real time as the data is being collected, or it may be stored in a memory unit or buffer and provided to the intelligence module after the experiment has been completed. Similarly, the data set may be provided to a separate system such as a desktop computer system or other computer system, via a network connection (e.g., LAN, VPN, intranet, Internet, etc.) or direct connection (e.g., USB or other direct wired or wireless connection) to the acquiring device, or provided on a portable medium such as a CD, DVD, floppy disk or the like. In certain aspects, the data set includes data points having a pair of coordinate values (or a 2-dimensional vector). For PCR data, the pair of coordinate values typically represents the cycle number and the fluorescence intensity value.

After cross-talk coefficients have been determined in step 130, the determined cross-talk coefficients may be applied to the original or a new PCR data set to produce a cross-talk corrected data set in step 140. In step 150, the cross-talk coefficients and/or cross-talk corrected PCR data set or other data may be stored to a memory unit, provided to a different system, e.g., over a network connection or via a portable storage medium, or displayed on a display device such as a monitor or printer.

Cross-Talk Coefficient Determination

In conventional cross-talk models, the cross-talk coefficients are typically calculated as follows:

Assume a single sample that contains two visible dyes with unique yet overlapping spectra. The detection system consists of two unique light spectra filters each of which passes about 95% of one dye spectra and about 5% of the other dye spectra. Each filter is typically optimized to pass light from only one dye. The light passed by each of the filters is considered to be channel one and two respectively.

(1) Take the average of five data points in the plateau signal region of channel 1 and 2:

$PLAvg1 = \text{average(five points plateau channel 1)}$ $PLAvg2 = \text{average(five points plateau channel 2)}$ (2) Compute the cross-talk coefficient for the sample:

$XT\text{-}dye2\text{-}channel1 = PLAvg2/PLAvg1$ (3) Now, increase the sample size to a 96 microwell plate and compute XT for channel 1->channel 2:

$XT(1\text{-}>2) = \text{average}(XT1, XT2, \ldots, XT96)$

This conventional method of calculating cross-talk is satisfactory providing that (1) a plateau exists, (2) the plateau is flat, and (3) there is minimum noise in the plateau. However, there are many data sets where this will not be the case.

According to various embodiments of the present invention, methods are provided for increasing the calculation accuracy of cross-talk coefficients. According to certain aspects, cross-talk coefficients are determined by using optimization techniques similar to linear regression. Defining "Signal" as the basis signal and "XTSignal" as the cross-talk signal, subscript i as the cycle number, q as the multiplicative gain, r and s as the offset and slope, three exemplary embodiments can be described by the following equations:

(1) Minimize the sum of squares between each fluorescent signal and cross-talk signal using a simple gain "q" as shown in Equation (1) below.

$$\min[\Sigma_i(XT\text{Signal}_i - q*\text{Signal}_i)^2] \qquad (1)$$

(2) Minimize the sum of squares between each fluorescent signal and cross-talk signal using a common offset "r", and slope "s" but an individual simple gain "q" as shown in Equation (2) below. This would result in cross-talk coefficient for each channel and a common linear term for all channels.

$$\min\left[\sum_{i}\begin{bmatrix}(XTSignal1_i-(r+s*i+q1*Signal_i))^2+\\(XTSignal2_i-(r+s*i+q2*Signal_i))^2+\\(XTSignal3_i-(r+s*i+q3*Signal_i))^2\end{bmatrix}\right] \quad (2)$$

(3) Minimize the sum of squares between each fluorescent signal and cross-talk signal using an offset "r", slope "s" and simple gain "q" as shown in Equation (3) below. This would result in a cross-talk coefficient and linear term for each channel.

$$\min[\Sigma_i(XTSignal_i-(r+s*i+q*Signal_i))^2] \quad (3)$$

In other aspects, a sum of the absolute values of the difference between the PCR data set and the cross-talk data set is minimized. Other minimization methods may be used, such as for example, Levenberg-Marquardt methods, Linear Programming methods, Nelder-Mead methods, gradient descent methods, sub-gradient methods, simplex methods, ellipsoid methods, bundle methods, Newton's method, quasi-Newton methods, interior point methods and other methods as would be apparent to one skilled in the art.

One advantage of these various embodiments is that data across the entire signal acquisition range is used to determine cross-talk coefficients. For example, all data across the acquisition range may be used, or portions of data across the entire acquisition range may be used. This provides for crosstalk coefficients that average out systematic data acquisition errors. In contrast, conventional methods rely exclusively on the plateau region which contains less than 10% of the data. The embodiments of the present invention also provide additional advantages for assays such as PCR. During PCR, the plateau region signal is generated when the majority of the probes have been consumed. For this reason, a baseline signal threshold is typically employed for target identification. Therefore, the conventional methods use a noisy signal to determine cross-talk coefficients with limited information that does not include data from the true signal acquisition point on the curve. Also, incorrect assumptions used in conventional crosstalk models have also been found to induce errors as a function of the data acquisition curve. Using the entire curve for cross talk calculation removes some of these erroneous assumptions. The farther use of correct models also virtually eliminates the crosstalk correction errors.

According to certain aspects, a background and/or baseline subtraction is performed on the data sets representing all signals (basis signal and cross-talk signals) prior to determining the cross-talk coefficients. A background subtraction is typically done by subtracting a buffer signal unique for each channel. A baseline subtraction is typically done by defining a baseline (e.g., slope and intercept) and subtracting this baseline from all signal values (basis signal and crosstalk signal). The baseline can be defined by specifying a baseline start and stop value and performing a linear regression between these endpoints, or by curve fitting a function (such as a double sigmoid function) and using the slope and intercept parameters from this function as the baseline. According to certain aspects, outlier points or "spikes" are removed from the data sets (signals) before determining cross-talk coefficients. U.S. patent application Ser. Nos. 11/316,315, titled "Levenberg Marquardt Outlier Spike Removal Method," filed on Dec. 20, 2005, and Ser. No. 11/349,550, titled "PCR Elbow Determination By Use of a Double Sigmoid Function Curve Fit With the Levenberg-Marquardt Algorithm and Normalization," filed on Feb. 6, 2006, which are each hereby incorporated by reference in its entirety, disclose techniques for fitting a double sigmoid function to determine, inter alia, slope and intercept parameters for PCR curves, and also for identifying and removing outlier points or "spikes" in a PCR data set.

Example Using HPV Calibration Assay

Consider a specific two-channel case: the FAM signal and its cross-talk into the HEX channel in an HPV calibration assay as shown in FIGS. 2A and 2B. FAM and HEX are well known fluorescent dyes having different excitation and emission characteristics. The signals in FIGS. 2A and 2B are nearly ideal, in that there is a well defined flat plateau with little noise. Thus, one would expect the cross-talk coefficients to be nearly equal as calculated with the conventional method and the methods of equations (1)-(3).

Analysis Using the Conventional Methodology of Determining Cross-Talk Coefficients:

Take the average of five points in the plateau region from cross-talk data and divide by the average of five points in the plateau region from the pure signal. The cross-talk coefficient is then defined as the mean of the cross-talk coefficient for all wells in the thermal cycler. The results are (shown via Mathematica® code):

```
TableMean = 0*Range[24];
For[j = 1, j ≦ 24, j ++,
   TableMean[[j]] = Mean[Table[FC1[[60 + i, j]], {i, 50, 55}]]/
      Mean[Table[FC1[[i, j]], {i, 50, 55}]];
]
TableMean
{0.0173338, 0.0171016, 0.016073, 0.015443, 0.0165934, 0.0181777,
 0.0170146, 0.0155421, 0.0166653, 0.0145379, 0.0150514, 0.014366,
 0.0160809, 0.0152727, 0.0147269, 0.0134197, 0.0135746, 0.0133044,
 0.0158858, 0.0163226, 0.0159318, 0.0148446, 0.0139202, 0.0146015}
MTM = Mean[TableMean]
0.0154911
```

Thus, in this example, the FAM to HEX cross-talk coefficient is determined to be 0.01549. A summary of the FAM to HEX cross-talk coefficient for the methods of equations (1)-(3) is shown in Table 1 below:

TABLE 1

| Calculation Method | Cross-Talk Coefficient | Offset | Linear Term |
|---|---|---|---|
| Existing | 0.01549 | — | — |
| Equation 1 | 0.01572 | — | — |
| Equation 2 | 0.01470 | 0.03947 | −0.00011043 |
| Equation 3 | 0.01433 | 0.03132 | 0.00040327 |

Equation 1, which is perhaps most similar to the Conventional Method, produces a nearly identical cross-talk coefficient, whereas the Equations 2 and 3 differ, since they include a linear term.

Comparison of Cross-Talk Matrices: Conventional Method and Equation (1)

Consider a specific four-channel case: it is instructive to compare all of the cross-talk coefficients for FAM, HEX, JA270, and CY5.5 in an HPV calibration assay. Shown in Table 2 below are the cross-talk coefficients calculated using the conventional method, whereas in Table 3 is shown the coefficients calculated using Equations (1)-(3). Equation (1) does not use the diagonal elements ($a_{11}, a_{22}, a_{33}, a_{44}$), so these cells are marked as "—". As discussed above for this HPV calibration set, containing a well-defined flat plateau with minimal noise, the two sets of cross-talk coefficients are expected to be nearly identical.

TABLE 2

Existing Cross-Talk Matrix:

|  | FAM | HEX | JA270 | CY5.5 |
|---|---|---|---|---|
| FAM Filter | 0.9828 | 0.0023 | 0.0016 | 0.0014 |
| HEX Filter | 0.0153 | 0.9970 | 0.0055 | 0.0019 |
| JA270 Filter | 0.0008 | 0.0005 | 0.9876 | 0.0027 |
| CY5.5 Filter | 0.0012 | 0.0002 | 0.0053 | 0.9940 |

TABLE 3

Cross-Talk Matrix Calculated using Equation 1:

|  | FAM | HEX | JA270 | CY5.5 |
|---|---|---|---|---|
| FAM Filter | — | 0.0024 | 0.0020 | 0.0021 |
| HEX Filter | 0.0157 | — | 0.0063 | 0.0027 |
| JA270 Filter | 0.0013 | 0.0005 | — | 0.0032 |
| CY5.5 Filter | 0.0016 | 0.0003 | 0.0056 | — |

Thus, any difference in applying the conventional method vs. the methods of Equations (1)-(3), in this particular example, would be due to the mathematical application of the cross-talk coefficients, not the coefficients themselves. It should be noted, however, that there are many examples where the cross-talk coefficients are very different when the current method is compared with Equations (1)-(3).

Application of Cross-Talk Coefficients to Produce Cross-Talk Corrected Data

The conventional method of applying cross-talk coefficients assumes an additive linear model shown in equations (4) below:

$$f_1 = a_{11}c_1 + a_{12}c_2 + a_{13}c_3 + a_{14}c_4$$

$$f_2 = a_{21}c_1 + a_{22}c_2 + a_{23}c_3 + a_{24}c_4$$

$$f_3 = a_{31}c_1 + a_{32}c_2 + a_{33}c_3 + a_{34}c_4$$

$$f_4 = a_{41}c_1 + a_{42}c_2 + a_{43}c_3 + a_{44}c_4 \quad (4)$$

where $f_i$ is the measured signal, $c_i$ is the fluorescent dye signal, and $a_{IJ}$ is the cross talk from channel J to channel I.

These cross-talk coefficients also have the property that $$\sum_I a_{IJ} = 1 \quad (5)$$

The set of equations (4) can be solved by matrix inversion to yield the dye signal $c_i$, which is defined as the cross-talk corrected signal. One problem with this approach is that it assumes that all of the signal from channel J is parsed between channels (1,2,3,4). This, in general, is not true.

According to one embodiment, cross-talk coefficients are applied using a subtractive linear model to produce cross-talk corrected data sets. A linear subtractive model for Equation (1) is shown in equations (6) below:

$$f_{1C} = f_1 - (a_{12}f_2 + a_{13}f_3 + a_{14}f_4)$$

$$f_{2C} = f_2 - (a_{21}f_1 + a_{23}f_3 + a_{24}f_4)$$

$$f_{3C} = f_3 - (a_{31}f_1 + a_{32}f_2 + a_{34}f_4)$$

$$f_{4C} = f_4 - (a_{41}f_1 + a_{42}f_2 + a_{43}f_3) \quad (6)$$

where $f_i$ is the measured fluorescence in channel (i) and $f_{iC}$ is the cross-talk corrected signal in channel (i). The coefficients $a_{IJ}$ denote the cross talk coefficients from channel (J) to channel (I). This model makes no assumptions on the parsing of the basis signal amongst different channels.

A linear subtractive model for Equation (2) is shown in equations (7) below:

$$f_{1C} = f_1 - (a_{12}f_2 + a_{13}f_3 + a_{14}f_4) - (r + s*i)$$

$$f_{2C} = f_2 - (a_{21}f_1 + a_{23}f_3 + a_{24}f_4) - (r + s*i)$$

$$f_{3C} = f_3 - (a_{31}f_1 + a_{32}f_2 + a_{34}f_4) - (r + s*i)$$

$$f_{4C} = f_4 - (a_{41}f_1 + a_{42}f_2 + a_{43}f_3) - (r + s*i) \quad (7)$$

where $f_i$ is the measured fluorescence in channel (i) and $f_{iC}$ is the cross-talk corrected signal in channel (i). The coefficients $a_{IJ}$ denote the cross talk coefficients from channel (J) to channel (I). Equation (7) uses a gain and linear term, r and s, that are common for all channels.

A linear subtractive model for Equation (3) is shown in equations (8) below:

$$f_{1C} = f_1 - (a_{12}f_2 + a_{13}f_3 + a_{14}f_4) - (r_1 + s_1*i)$$

$$f_{2C} = f_2 - (a_{21}f_1 + a_{23}f_3 + a_{24}f_4) - (r_2 + s_2*i)$$

$$f_{3C} = f_3 - (a_{31}f_1 + a_{32}f_2 + a_{34}f_4) - (r_3 + s_3*i)$$

$$f_{4C} = f_4 - (a_{41}f_1 + a_{42}f_2 + a_{43}f_3) - (r_4 + s_4*i) \quad (8)$$

where $f_i$ is the measured fluorescence in channel (i) and $f_{iC}$ is the cross-talk corrected signal in channel (i). The coefficients $a_{IJ}$ denote the cross talk coefficients from channel (J) to channel (I). Equation (8) uses a gain and linear term, r and s, that are different in each channel.

Also note that calculation of these cross-talk corrected signals advantageously does not require matrix inversion. Also, in certain aspects, equations (6)-(8) may be modified by first subtracting a background or baseline from both the basis and cross-talk signals.

Comparison of Cross-Talk Application in Two Dye Situation

Figure 3:
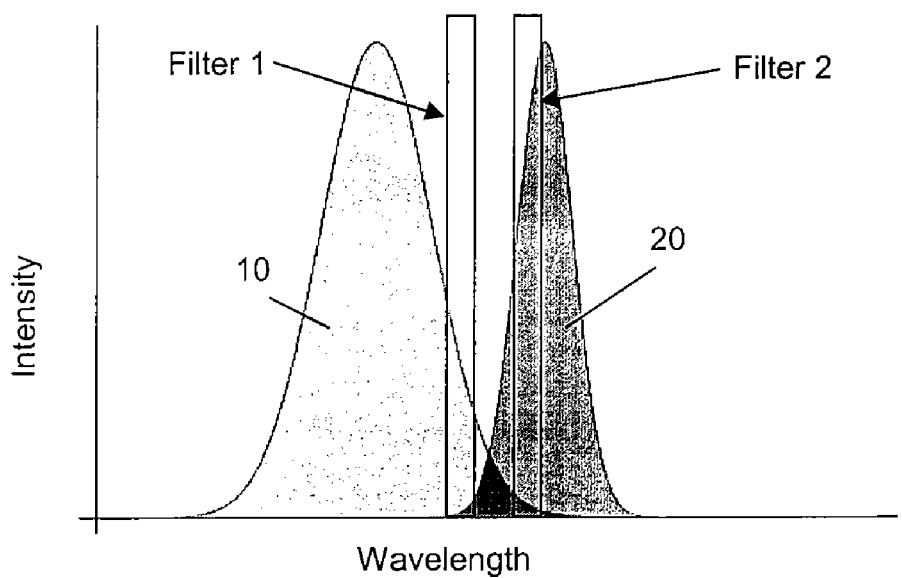
FIG. 3 illustrates overlap of two dye spectra in two filter ranges.

Consider the dye spectra shown in FIG. 3, where the spectra 10 represents dye 1 (FAM) and the spectra 20 represents dye 2 (HEX). It is desired to remove the cross-talk, represented by the overlap region in the FAM and HEX dyes.

In the conventional method, solving equations (4) and (5) above gives the results shown in equations (9) and (10), below, for the cross-talk corrected signal for FAM as observed within Filter 1 and HEX as observed within Filter 2 respectively.

$$c_1 = \frac{f_1(1 - a_{12}) - a_{12}f_2}{1 - a_{12} - a_{21}} \quad (9)$$

$$c_2 = \frac{f_2(1 - a_{21}) - a_{21}f_1}{1 - a_{12} - a_{21}} \quad (10)$$

The cross-talk corrected signal using Equation (1) for this system is given as equations (11) and (12) below:

$$f_{1C} = f_1 - a_{12}f_2 \quad (11)$$

$$f_{2C} = f_2 - a_{21}f_1 \quad (12)$$

Equation (11) overcomes two problems associated with equation (9), namely the $(1-a_{12})$ multiplier to $f_1$, which causes cross-talk over-compensation, is no longer present, and an incorrect denominator is no longer present.

Comparison of Conventional Vs. New Methods on HPV Data Set

A HPV data set, with just FAM and HEX channels was tested using the existing method and Equations (1)-(3). This data contained target in the FAM channel and no target in the HEX channel. These methods were applied to the cross-talk signal in the HEX channel and the resultant residual plots were examined. Ideally, the residuals would center around a zero intercept with zero slope.

a) Residual Plots Using Conventional Method

Figure 4:
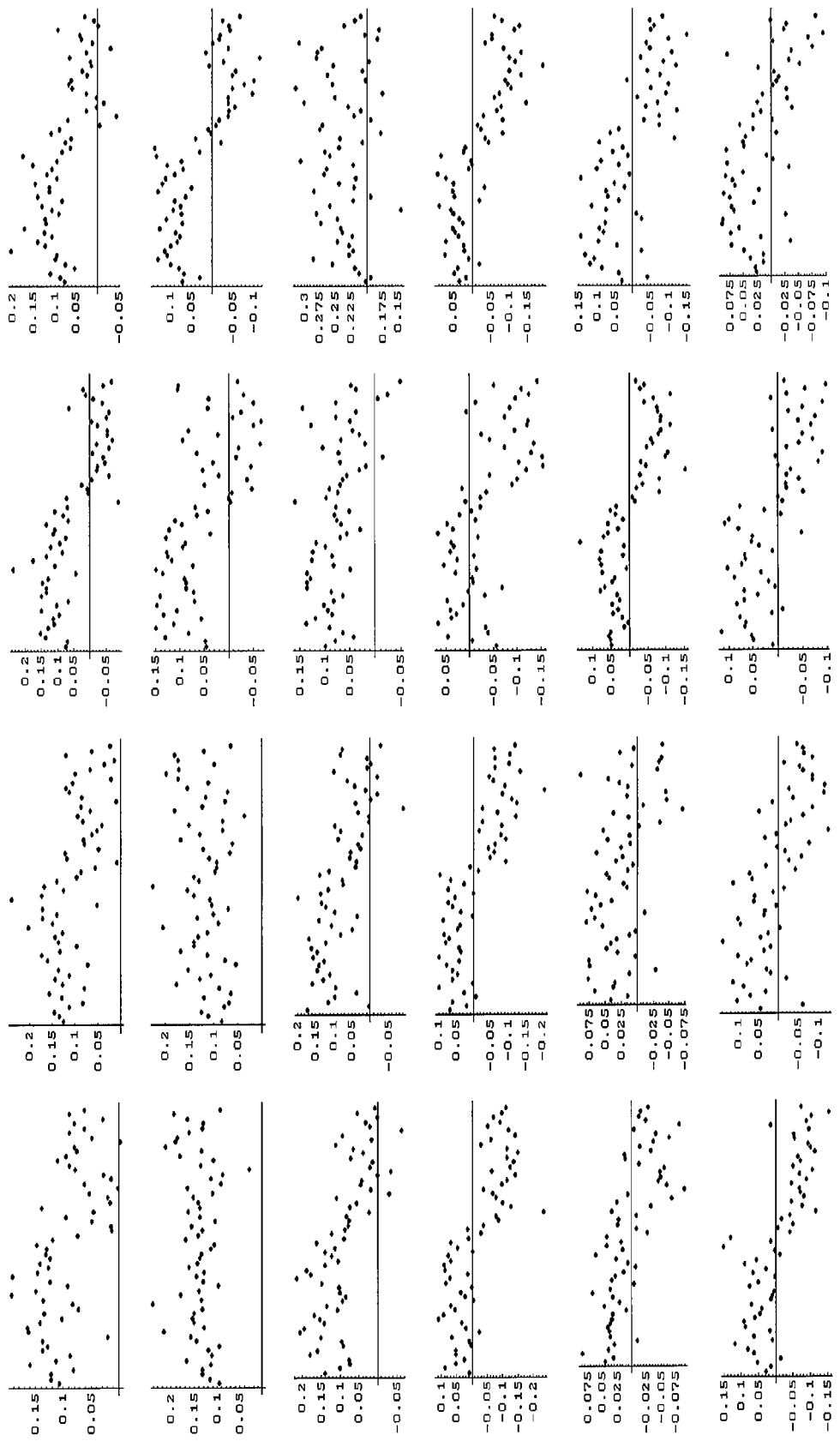
FIG. 4 shows 24 individual residual plots when FAM and HEX channels were tested using the conventional method with target in the FAM channel and no target in the HEX channel.

FIG. 4 shows the 24 individual residual plots, whereas FIG. 5 shows the twenty-four plots end-to-end. FIG. 6 shows a superposition of all twenty-four plots. In an optimal correction, one would expect that the residuals center around the x-axis with a slope and intercept of zero. In FIG. 4, however, the majority of the graphs show that the residuals decrease substantially from cycle 1 to cycle 60, indicating a non-optimal cross-talk implementation.

In observing FIG. 6 (the superposition of all 24 graphs of FIG. 4), it is clear that there is a significant declining trend from cycle 1 to cycle 60, when using the conventional cross-talk method.

b) Residual Plots Using the Equations (1) to (3).

FIGS. 7-9 show the end-to-end residual plots for Equations (1)-(3), respectively. Likewise, FIGS. 10-12 show the superimposed residual plots of Equations (1)-(3). Comparing FIG. 6 with FIGS. 10-12, it is apparent that range of the residuals using the techniques of the present invention are advantageously smaller than the conventional method. In addition, using the techniques of the present invention, the trend lines of the superimposed plots have slopes and intercepts much closer to the goal of zero. In this example, the FAM and HEX cross-talk was about 2%. Thus, these plots show a more optimal correction, indicating the robustness of the techniques of the present invention. The superiority of the techniques of the present invention will become even more apparent in examples where there are more dyes present and the cross-talk is in the range of 2-20%.

Comparison of Conventional Vs. New Methods on HIV Data Set

Figure 13:
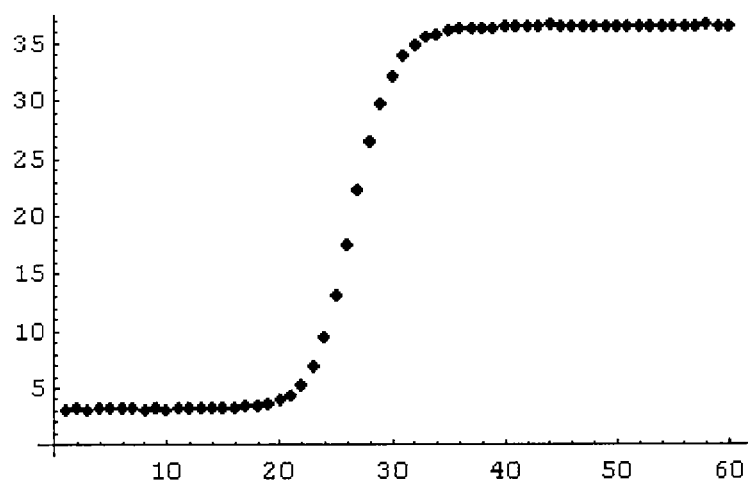
FIG. 13 shows a data set for a PCR experiment of an HIV assay with the target in the FAM filter and no target in the HEX filter.
Figure 14:
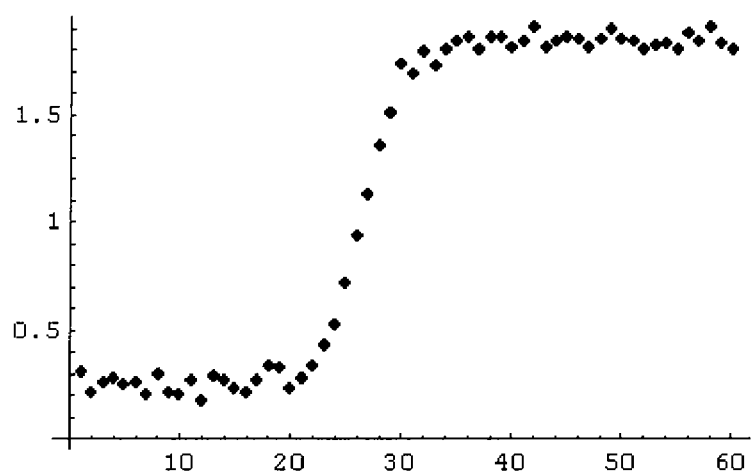
FIG. 14 shows a crosstalk data set for the HEX channel corresponding to the HIV assay of FIG. 13.

A PCR experiment of an HIV assay with the target in the FAM filter and no target in the HEX filter is shown in FIGS. 13 and 14 for the FAM and HEX filters respectively. Using the data in FIGS. 13 and 14, the cross-talk coefficient for the FAM->HEX cross-talk ($a_{21}$) is calculated to be $a_{21}$=0.051 for both the Conventional method and Equation (1).

Figure 17:
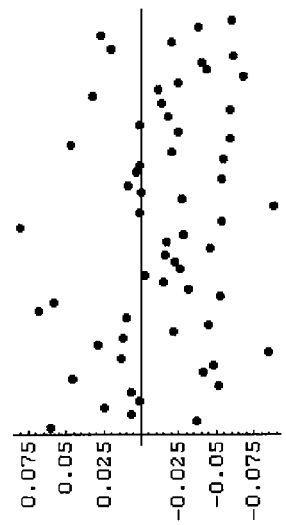
FIGS. 15, 16, and 17 show the cross-talk corrected signal in the HEX channel using the conventional method, and two embodiments of the present invention, respectively.
Figure 16:
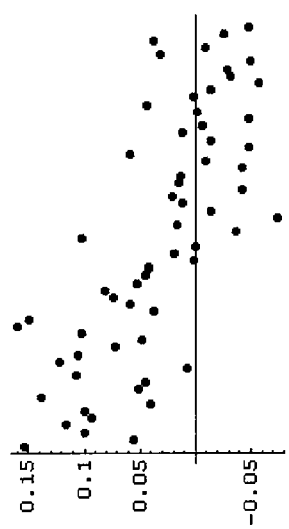
Figure 15:
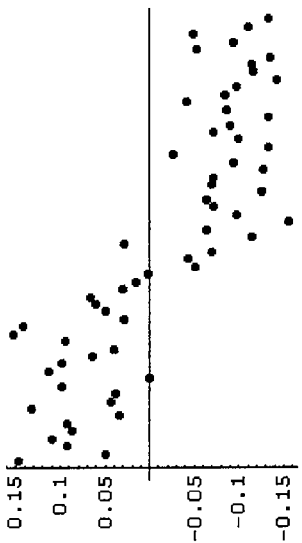

FIGS. 15, 16, and 17 show the cross-talk corrected signal in the HEX channel using the conventional method, Equation (1) and Equation (3), respectively. It is seen that the over correction of the signals is greatly reduced using either of the latter two methods.

It should be appreciated that the cross-talk coefficient determination processes, including the cross-talk correction processes, described herein may be implemented in computer code running on a processor of a computer system. The code includes instructions for controlling a processor to implement various aspects and steps of the processes. The code is typically stored on a hard disk, RAM or portable medium such as a CD, DVD, etc. Similarly, the processes may be implemented in a PCR device such as a thermocycler including a processor executing instructions stored in a memory unit coupled to the processor. Code including such instructions may be downloaded to the PCR device memory unit over a network connection or direct connection to a code source or using a portable medium as is well known.

One skilled in the art should appreciate that the cross-talk coefficient determination and cross-talk correction processes of the present invention can be coded using a variety of programming languages such as C, C++, C#, Fortran, VisualBasic, etc., as well as applications such as Mathematica® which provide pre-packaged routines, functions and procedures useful for data visualization and analysis. Another example of the latter is MATLAB®.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A method of determining cross-talk coefficients for a Polymerase Chain Reaction (PCR) optical detection system having at least two optical elements, each optical element operable to isolate a different specific electromagnetic wavelength range, the method comprising the steps, implemented in a processor, of:

receiving, for each optical element, a PCR data set acquired over a data acquisition range of a PCR growth process, wherein the data acquisition range represents a plurality of PCR cycles, and wherein each PCR data set includes a data value for each PCR cycle in the acquisition range;

receiving, for each other optical element, a cross-talk data set acquired over the acquisition range simultaneously with the PCR data set, and wherein each cross-talk data set includes a data value for each PCR cycle in the acquisition range; and determining cross-talk coefficients using the PCR and cross-talk data sets over the acquisition range, wherein determining includes, for each optical element, minimizing a sum of the squares between each PCR data set and cross-talk data set over the acquisition range using an equation of the form:

$$\min\left[\sum_i (XTSignal_i - q*Signal_i)^2\right],$$

wherein i is a PCR cycle number, wherein $Signal_i$ is the PCR data value for cycle i for each optical element, wherein $XTSignal_i$ is the cross-talk data value for cycle i for each other optical element, and wherein q is a multiplicative gain factor.

2. The method of claim 1, wherein the acquisition range includes a baseline region, a growth region and a plateau region.

3. The method of claim 1, wherein the data acquisition range represents a plurality of PCR cycles, and wherein determining cross-talk coefficients includes minimizing a sum of the absolute values between each PCR data set and cross-talk data set over the acquisition range.

4. A method of determining cross-talk coefficients for a Polymerase Chain Reaction (PCR) optical detection system having at least two optical elements, each optical element operable to isolate a different specific electromagnetic wavelength range, the method comprising the steps, implemented in a processor, of:

receiving, for each optical element, a PCR data set acquired over a data acquisition range of a PCR growth process, wherein the data acquisition range represents a plurality of PCR cycles, and wherein each PCR data set includes a data value for each PCR cycle in the acquisition range;

receiving, for each other optical element, a cross-talk data set acquired over the acquisition range simultaneously with the PCR data set, and wherein each cross-talk data set includes a data value for each PCR cycle in the acquisition range; and determining cross-talk coefficients using the PCR and cross-talk data sets over the acquisition range, wherein determining includes, for each optical element, minimizing a sum of the squares between each PCR data set and cross-talk data set over the acquisition range using an equation of the form:

$$\min\left[\sum_i \begin{bmatrix} (XTSignal1_i - (r+s*i+q1*Signal_i))^2 + \\ (XTSignal2_i - (r+s*i+q2*Signal_i))^2 + \\ (XTSignal3_i - (r+s*i+q3*Signal_i))^2 \end{bmatrix}\right]$$

wherein i is a PCR cycle number, wherein $Signal_i$ is the PCR data value for cycle for each optical element, wherein $XTSignal_i$ is the cross-talk data value for cycle i for each other optical element, wherein r is a common offset, wherein s is a common slope and wherein q1, q2 and q3 are multiplicative gain factors.

5. A method of determining cross-talk coefficients for a Polymerase Chain Reaction (PCR) optical detection system having at least two optical elements, each optical element operable to isolate a different specific electromagnetic wavelength range, the method comprising the steps, implemented in a processor, of:

receiving, for each optical element, a PCR data set acquired over a data acquisition range of a PCR growth process, wherein the data acquisition range represents a plurality of PCR cycles, and wherein each PCR data set includes a data value for each PCR cycle in the acquisition range;

receiving, for each other optical element, a cross-talk data set acquired over the acquisition range simultaneously with the PCR data set, and wherein each cross-talk data set includes a data value for each PCR cycle in the acquisition range; and determining cross-talk coefficients using the PCR and cross-talk data sets over the acquisition range, wherein determining includes, for each optical element, minimizing a sum of the squares between each PCR data set and cross-talk data set over the acquisition range using an equation of the form:

$$\min\left[\sum_i (XTSignal_i - (r+s*i+q*Signal_i))^2\right],$$

wherein i is a PCR cycle number, wherein $Signal_i$ is the PCR data value for cycle i for each optical element, wherein $XTSignal_i$ is the cross-talk data value for cycle i for each other optical element, wherein r is an offset, wherein s is a slope and wherein q is a multiplicative gain factor.

6. The method of claim 1, further including:
determining a baseline for each PCR data set and each cross-talk data set; and
prior to determining cross-talk coefficients, subtracting the respective baseline from each data set.

7. The method of claim 6, wherein determining a baseline includes performing a linear regression on a data set between defined baseline start and baseline stop positions.

8. The method of claim 6, wherein determining a baseline includes curve fitting a double sigmoid function to identify slope and intercept values.

9. The method of claim 1, further including removing outlier points from one or more of the PCR data sets and cross-talk data sets prior to determining cross-talk coefficients.

10. The method of claim 1, wherein the optical elements include one or more filters, each filter allowing light of a different specific wavelength range to pass.

11. The method of claim 10, wherein the optical elements include at least four filters.

12. The method of claim 1, further including:
applying the determined cross-talk coefficients to a PCR data set using a linear subtractive model to produce a cross-talk corrected data set.

13. The method of claim 12, wherein the linear subtractive model includes an equation of the form:

$$f_{iC} = f_i - \left(\sum_{j\neq i} a_{ij} f_j\right)$$

where $f_i$ is the measured signal in channel (i) and $f_{iC}$ is the cross-talk corrected signal in channel (i), and where the coefficients $a_{ij}$ denote the cross-talk coefficients from channel (j) to channel (i).

14. The method of claim 12, wherein the linear subtractive model includes an equation of the form:

$$f_{iC} = f_i - \left(\sum_{j\neq i} a_{ij} f_j\right) - (r + s*i)$$

where $f_i$ is the measured signal in channel (i) and $f_{iC}$ is the cross-talk corrected signal in channel (i), where the coefficients $a_{ij}$ denote the cross talk coefficients from channel (j) to channel (i), and where r and s are a gain and a linear term, respectively, that are common for all channels (i).

15. The method of claim 12, wherein the linear subtractive model includes an equation of the form:

$$f_{iC} = f_i - \left(\sum_{j\neq i} a_{ij} f_j\right) - (r_i + s_i*i)$$

where $f_i$ is the measured signal in channel (i) and $f_{iC}$ is the cross-talk corrected signal in channel (i), where the coefficients $a_{ij}$ denote the cross talk coefficients from channel (j) to channel (i), and where $r_i$ and $s_i$ are a gain and a linear term, respectively, that are different for each channel (i).

16. The method of claim 1, further including displaying or outputting the determined crosstalk coefficients.

17. The method of claim 1, further including storing the determined cross-talk coefficients to a memory module for later use in producing cross-talk corrected data sets.

18. A tangible computer readable medium that stores code for controlling a processor to determine cross-talk coefficients for a Polymerase Chain Reaction (PCR) optical detection system having at least two optical elements, each optical element operable to isolate a different specific electromagnetic wavelength range, the code including instructions to:
receive, for each optical element, a PCR data set acquired over a data acquisition range of a PCR growth process, the acquisition range including a baseline region, a growth region and a plateau region, wherein the data acquisition range represents a plurality of PCR cycles, and wherein each PCR data set includes a data value for each PCR cycle in the acquisition range;

receive, for each other optical element, a cross-talk data set for each filter acquired over the acquisition range simultaneously with the PCR data set, wherein each cross-talk data set includes a data value for each PCR cycle in the acquisition range; and determine cross-talk coefficients using the PCR and cross-talk data sets over the acquisition range, wherein the instructions to determine include instructions to minimize, for each optical element, a sum of the squares between each PCR data set and cross-talk data set over the acquisition range using an equation of the form:

$$\min\left[\sum_i (XTSignal_i - q*Signal_i)^2\right],$$

wherein i is a PCR cycle number, wherein $Signal_i$ is the PCR data value for cycle i for each optical element, wherein $XTSignal_i$ is the cross-talk data value for cycle i for each other optical element, and wherein q is a multiplicative gain factor.

19. A kinetic Polymerase Chain Reaction (PCR) system, comprising:

an optical detection module having at least two optical elements, each optical element operable to isolate a different specific electromagnetic wavelength range, wherein said optical detection module is adapted to:
  acquire, for each optical element, a PCR data set over a data acquisition range of a PCR growth process, the acquisition range including a baseline region, a growth region and a plateau region, wherein the data acquisition range represents a plurality of PCR cycles, and wherein each PCR data set includes a data value for each PCR cycle in the acquisition range; and
  simultaneously acquire, for each other optical element, a cross-talk data set over the acquisition range, wherein each cross-talk data set includes a data value for each PCR cycle in the acquisition range; and
an intelligence module adapted to process the acquired PCR data sets and cross-talk data sets to determine cross-talk coefficients using the PCR and cross-talk data sets over the acquisition range by minimizing, for each optical element, a sum of the squares between each PCR data set and cross-talk data set over the acquisition range using an equation of the form:

$$\min\left[\sum_i (XTSignal_i - q*Signal_i)^2\right],$$

wherein i is a PCR cycle number, wherein $Signal_i$ is the PCR data value for cycle i for each optical element, wherein $XTSignal_i$ is the cross-talk data value for cycle i for each other optical element, and wherein q is a multiplicative gain factor.

20. A nucleic acid melting analysis system, comprising:

an optical detection module having at least two optical elements, each optical element operable to isolate a different specific electromagnetic wavelength range, wherein said optical detection module is adapted to:
  acquire, for each optical element, a melting data set over a temperature acquisition range, and simultaneously acquire, for each other optical element, a cross-talk data set over the temperature acquisition range, wherein each melting data set includes a data value for each temperature in the temperature acquisition range, and wherein each cross-talk data set includes a data value for each temperature in the temperature acquisition range; and
  determine cross-talk coefficients by minimizing, for each element, a sum of squares between each melting data set and cross-talk data set over the acquisition range by minimizing a sum of the squares between each melting data set and cross-talk data set over the temperature acquisition range using an equation of the form:

$$\min\left[\sum_i (XTSignal_i - q*Signal_i)^2\right],$$

wherein i is a temperature index, wherein $Signal_i$ is the melting data value for temperature index i for each optical element, wherein $XTSignal_i$ is the cross-talk data value for temperature index i for each other optical element, and wherein q is a multiplicative gain factor.

21. A method of determining cross-talk coefficients for an optical detection system having at least two optical elements, each optical element operable to isolate a different specific electromagnetic wavelength range, the method comprising the steps, implemented in a processor, of:

receiving, for each optical element, a first data set acquired over a data acquisition range of a growth process, wherein the data acquisition range represents a plurality of cycles, wherein each first data set includes a data value for each cycle in the acquisition range;

receiving, for each other optical element, a cross-talk data set acquired over the acquisition range simultaneously with the first data set, and wherein each cross-talk data set includes a data value for each cycle in the acquisition range; and determining cross-talk coefficients using the first and cross-talk data sets over the acquisition range by minimizing, for each optical element, a sum of the squares between each first data set and cross-talk data set over the acquisition range using an equation of the form:

$$\min\left[\sum_i (XTSignal_i - q*Signal_i)^2\right],$$

wherein i is a cycle number, wherein $Signal_i$ is the data value of the first data set for cycle i for each optical element, wherein $XTSignal_i$ is the cross-talk data value for cycle i for each other optical element, and wherein q is a multiplicative gain factor.

* * * * *